(12) United States Patent
Fraser et al.

(10) Patent No.: US 9,981,671 B2
(45) Date of Patent: May 29, 2018

(54) RAILWAY INSPECTION SYSTEM

(75) Inventors: Randy Scott Fraser, Yorktown Heights, NY (US); Patrick Michael Graham, Watertown, CT (US); Paul Sanders Underwood, Bridgewater, CT (US)

(73) Assignee: NORDCO INC., Oak Creek, WI (US)

( * ) Notice: Subject to any disclaimer, the term of this patent is extended or adjusted under 35 U.S.C. 154(b) by 934 days.

(21) Appl. No.: 13/409,487

(22) Filed: Mar. 1, 2012

(65) Prior Publication Data
US 2013/0231873 A1 Sep. 5, 2013

(51) Int. Cl.
*B61K 5/00* (2006.01)
*B61L 23/04* (2006.01)

(52) U.S. Cl.
CPC ............... *B61K 5/00* (2013.01); *B61L 23/04* (2013.01); *B61L 23/042* (2013.01); *B61L 23/044* (2013.01); *B61L 23/045* (2013.01); *B61L 23/047* (2013.01); *G01N 2291/2623* (2013.01)

(58) Field of Classification Search
CPC .. B61K 5/00; G01N 2291/2623; B61L 23/042
USPC ................... 702/35, 182, 183, 184
See application file for complete search history.

(56) References Cited

U.S. PATENT DOCUMENTS

| | | | |
|---|---|---|---|
| 4,391,134 A * | 7/1983 | Theurer et al. | 73/146 |
| 5,386,727 A * | 2/1995 | Searle | G01N 29/2493 73/602 |
| 5,648,904 A * | 7/1997 | Scott | 701/117 |
| 5,791,063 A * | 8/1998 | Kesler | E01B 35/00 33/1 Q |
| 5,837,880 A | 11/1998 | Shakinovsky et al. | |
| 5,867,404 A * | 2/1999 | Bryan | B61K 9/08 342/457 |
| 5,956,664 A | 9/1999 | Bryan | |
| 5,970,438 A | 10/1999 | Clark et al. | |
| 5,978,717 A | 11/1999 | Ebersohn et al. | |
| 6,055,862 A | 5/2000 | Martens | |
| 6,064,428 A | 5/2000 | Trosino et al. | |
| 6,356,299 B1 | 3/2002 | Trosino et al. | |
| 6,476,603 B2 | 11/2002 | Clark et al. | |
| 6,570,497 B2 | 5/2003 | Puckette, IV et al. | |
| 6,594,591 B2 | 7/2003 | Clark et al. | |
| 6,600,999 B2 | 7/2003 | Clark et al. | |

(Continued)

*Primary Examiner* — Michael Dalbo
(74) *Attorney, Agent, or Firm* — Greer, Burns & Crain, Ltd.

(57) ABSTRACT

A railway inspection system for monitoring defects of a rail, including an inspection vehicle configured for traversing the rail, a sensor disposed on the vehicle configured for obtaining rail condition data, a memory disposed on the vehicle and storing previous rail condition data from a previous traversal of the rail, a display device disposed on the vehicle, a processor disposed on the vehicle and a non-transitory computer-readable medium disposed on the vehicle and containing instructions, which when executed by the processor, cause performance of the following steps in real-time as the vehicle traverses the rail, namely obtaining current rail condition data from the sensor, displaying on the display device representative images of the current rail condition data, retrieving the previous rail condition data from the memory, and displaying on the display device representative images of the previous rail condition data.

8 Claims, 10 Drawing Sheets

(56) References Cited

U.S. PATENT DOCUMENTS

| | | | |
|---|---|---|---|
| 7,616,329 B2 | 11/2009 | Villar et al. | |
| 7,755,660 B2 | 7/2010 | Nejikovsky et al. | |
| 7,849,748 B2 | 12/2010 | Havira | |
| 7,882,742 B1 | 2/2011 | Martens | |
| 8,000,457 B2* | 8/2011 | Harper | 379/100.01 |
| 8,181,529 B2 | 5/2012 | Crocker et al. | |
| 8,305,567 B2* | 11/2012 | Hesser | E01B 35/00 356/237.1 |
| 8,365,604 B2 | 2/2013 | Kahn | |
| 8,418,563 B2 | 4/2013 | Wigh et al. | |
| 8,424,387 B2 | 4/2013 | Wigh et al. | |
| 8,485,035 B2 | 7/2013 | Wigh et al. | |
| 8,739,631 B2 | 6/2014 | Havira et al. | |
| 8,806,948 B2 | 8/2014 | Kahn et al. | |
| 8,820,166 B2 | 9/2014 | Wigh et al. | |
| 2002/0010531 A1* | 1/2002 | Hawthorne | B61L 3/002 701/19 |
| 2002/0029116 A1* | 3/2002 | Sills | G01N 29/348 702/39 |
| 2002/0099507 A1* | 7/2002 | Clark | B61K 9/10 702/36 |
| 2004/0263624 A1* | 12/2004 | Nejikovsky et al. | 348/148 |
| 2005/0068184 A1* | 3/2005 | Kane | B61L 15/009 340/576 |
| 2006/0065055 A1* | 3/2006 | Barshinger | B61K 9/10 73/609 |
| 2007/0163352 A1* | 7/2007 | Nielsen | B61K 9/10 73/668 |
| 2007/0208841 A1* | 9/2007 | Barone | B61L 15/0027 709/223 |
| 2007/0217670 A1* | 9/2007 | Bar-Am | B61K 9/08 382/141 |
| 2009/0015685 A1* | 1/2009 | Shulman | G01C 11/00 348/222.1 |
| 2009/0273788 A1 | 11/2009 | Nagle, II et al. | |
| 2009/0282923 A1 | 11/2009 | Havira | |
| 2009/0320603 A1 | 12/2009 | Crocker et al. | |
| 2010/0004804 A1 | 1/2010 | Anderson et al. | |
| 2010/0007551 A1* | 1/2010 | Pagliuco | B61K 9/08 702/189 |
| 2010/0078228 A1* | 4/2010 | Trautweiler et al. | 177/25.13 |
| 2010/0100511 A1* | 4/2010 | Hirose et al. | 706/12 |
| 2010/0289822 A1* | 11/2010 | Harrison | 345/619 |
| 2011/0043199 A1 | 2/2011 | Crocker | |
| 2011/0209549 A1 | 9/2011 | Kahn | |
| 2012/0218868 A1 | 8/2012 | Kahn et al. | |
| 2013/0047729 A1 | 2/2013 | Wigh et al. | |
| 2013/0047730 A1 | 2/2013 | Wigh et al. | |
| 2013/0152691 A1 | 6/2013 | Wigh et al. | |
| 2013/0220019 A1 | 8/2013 | Havira et al. | |
| 2013/0220020 A1 | 8/2013 | Wigh et al. | |
| 2014/0251015 A1 | 9/2014 | Havira et al. | |

* cited by examiner

RAILWAY INSPECTION SYSTEM

BACKGROUND

The present invention relates generally to railway inspection systems, and more particularly, to an improved railway inspection system for monitoring defects of rails on a railway in a real-time basis.

Rails are the fundamental components of a railway, and serve as the surface on which train and other rail vehicle wheels run. It is well recognized in the railway industry that rails develop defects, either during the manufacturing process or as a result of normal use and/or environmental conditions. Defects have varying levels of severity, and may include for example, transverse defects, vertical sheer or split head defects, or horizontal sheer or split head defects. While minor or moderate defects are initially less likely to cause such problems, they may develop into more severe defects over time, particularly if left unattended. Depending on the severity of the defect, it may be decided to repair or replace a respective section of track.

As such, it is typical in the industry to take measures to prevent, or at least reduce such railway problems through routine inspection and maintenance. To detect rail defects, ultrasonic testing has often been employed, wherein ultrasonic inspection devices are mounted upon rail-traversing vehicles for continuously emitting and monitoring ultrasonic signals. Throughout this process, the device gathers rail inspection data (based on the behavior of the signals) that is used to identify rail defects.

In traditional systems, a rail inspector traverses a rail on a vehicle equipped with an ultrasonic device and manually reviews live rail inspection data. Upon identifying a potential defect based on the rail inspection data, the rail inspector stops and exits the vehicle, inspects the potential defect, and then returns to the vehicle to manually mark the result of the inspection (e.g., with an indication of a defect type or an indication that the no defect was found). Thereafter, the rail inspector resumes traversing the rail and repeats the process described above. Due to the constant stopping and starting of the vehicle, this system is commonly referred to as a "stop-start" system. After the traversal is complete, a repair technician traverses the rail and makes the necessary repairs based on the rail inspector's manually marked results. While in most instances the repair technician follows behind the rail inspector, often the rail inspector's ability to identify defects exceeds the repair technician's ability to repair those defects, and therefore the rail inspector may be directed to stop identifying additional defects until the repair technician catches up. Such delay increases the risk that a defect will become more severe.

In other known, but more recent systems, the rail inspection data is stored in an electronic form on the vehicle and is sent offsite for analysis following the vehicle's traversal of the rail. As part of the offsite analysis, the rail inspection data may be compared to similar data obtained from a previous run of the same portion of the rail. Such a comparison enables an analyst to identify changes in rail conditions over time, thereby identifying portions of the rail that are deemed appropriate for further (e.g., physical) inspection and/or repair. Next, a rail inspector traverses and physically inspects the identified portions of the rail, and provides a report to the analyst, who may supplement or modify the rail condition data for use during a subsequent traversal of that portion of the rail. Thereafter, a repair technician traverses the rail again to make the necessary repairs. This process is labor intensive, given that two traversals of the track are required to determine which portions of the track require repair work. Further, the analyst's comparison of rail inspection data is complex and error prone given the difficulty required in "matching up" the appropriate portions of the rail inspection data of the previous and current traversal (i.e., such that a they both represent the same portion of the rail, thereby allowing for a proper comparison and identification of defect reoccurrences, changes, etc.).

SUMMARY

The above-listed shortcomings are improved or resolved by the present rail inspection system, which features a rail traversing vehicle having sensors for obtaining current rail condition data, and an onboard memory storing previous rail condition data (from previous traversals of the rail). Such a configuration provides for a real-time "run-on-run" comparison between previous and current rail inspection data, thereby removing the need for an offsite analysis and the subsequent second rail traversal to effectively monitor the condition of the rail.

The present rail inspection system also features a user acknowledgement request technique to ensure that users are properly monitoring the display device as the vehicle traverses the rail. More specifically, monitoring of defects or potential defects exceeding a certain level of severity cause the system to force a user to provide an acknowledgment through use of conditional halting of a portion of the system (e.g., when no user acknowledgment is received after the vehicle has traveled a predetermined length).

Another feature of the present rail inspection system includes sensors that obtain rail condition data by considering tolerance, gain value, and outside temperature measurements. Further, the rail inspection system features the use of a wireless communication device to transfer and store rail inspection data between a remote server and the memory, thereby allowing vehicles to be exchanged (e.g., due to a mechanical defect), while still being able to obtain the appropriate previous rail inspection data for an effective real-time "run-on-run" comparison of a given portion of a rail.

More specifically, a first embodiment of a railway inspection system for monitoring defects of a rail is provided, which includes an inspection vehicle configured for traversing the rail, a sensor disposed on the vehicle and configured for obtaining rail condition data, and a memory disposed on the vehicle and storing previous rail condition data from a previous traversal of the rail. The system further includes a display device, a processor, and a non-transitory computer-readable medium disposed on the vehicle. The computer-readable medium contains instructions, which when executed by the processor, causes performance of select steps in real-time as the vehicle traverses the rail. The steps include obtaining current rail condition data from the sensor, displaying on the display device representative images of the current rail condition data, retrieving the previous rail condition data from the memory, and displaying on the display device representative images of the previous rail condition data. Further, in the described system, the sensor, memory, display device, processor, and computer-readable medium are electronically connected.

In a second embodiment, a non-transitory computer-readable medium is provided for use with a rail inspection system vehicle configured for traversing a rail and having a rail sensor, a memory, a processor, and a display device. The computer-readable medium contains instructions, which when executed by the processor, causes performance of the select steps in real-time as the vehicle traverses the rail. The steps include obtaining current rail condition data from the sensor, displaying representative images of the current rail condition data on the display device, retrieving the previous rail condition data from the memory, and displaying on the display device representative images of the previous rail condition data.

In a third embodiment, a railway inspection system for monitoring defects of a rail is provided, and includes an inspection vehicle configured for traversing the rail, a sensor disposed on the vehicle and configured for obtaining rail condition data, and a memory disposed on the vehicle and storing previous rail condition data from a previous traversal of the rail. The system further includes a wireless communication dev ce, a display device, a processor, and a non-transitory computer-readable medium disposed on the vehicle. The computer-readable medium contains instructions, which when executed by the processor, causes performance of the select steps in real-time as the vehicle traverses the rail.

In the third embodiment, the steps include obtaining current rail condition data from the sensor, displaying representative images of the current rail condition data on the display device, retrieving the previous rail condition data from the memory, and displaying representative images of the previous rail condition data on the display device. The steps further include comparing the current rail condition data to known rail data patterns, comparing the current rail condition data to the previous rail condition data, identifying a current rail condition indicator based on one of the comparisons, and displaying on the display device an indicator marker corresponding to the current rail condition indicator. Further, in the third embodiment, the sensor, memory, display device, processor, wireless communication device, and computer-readable medium are electronically connected. In addition, the wireless communication device is configured for transferring previous rail inspection data between the memory and a remote server.

In a fourth embodiment, a railway inspection system for aligning and comparing rail condition data associated with a rail is provided, the system including an inspection vehicle configured for traversing the rail, a sensor disposed on the vehicle and configured for obtaining current rail condition data, a location device disposed on the vehicle and configured for obtaining current location data of the vehicle, and a memory disposed on the vehicle and storing previous rail condition data from a previous traversal of the rail, including associated previous location data.

In the fourth embodiment, the system further includes a processor disposed on the vehicle, and a non-transitory computer-readable medium, disposed on the vehicle, and containing instructions, which when executed by the processor, causes performance of the several steps in real-time as the vehicle traverses the rail.

In the fourth embodiment, the steps include obtaining current rail condition data from the sensor, comparing the current rail condition data with a rail data pattern to identify a realignment object, upon identifying a realignment object, obtaining associated location data from the location device, matching previous and current rail condition data representing the realignment object, and calculating a location offset value based on the difference between associated previous and current location data. The steps further include applying the location offset value in comparing previous and current rail condition data to identify an indicator associated with the rail.

In a fifth embodiment, a non-transitory computer-readable medium is provided for use with a rail inspection system vehicle configured for traversing a rail and having a rail sensor, a memory storing previous rail condition data and associated location data, and a processor. The medium contains instructions, which when executed by the processor, causes performance of the following steps in real-time as the vehicle traverses the rail:

In the fifth embodiment, the steps include obtaining current rail condition data from the sensor, comparing the current rail condition data with a rail data pattern to identify a realignment object, upon identifying a realignment object, obtaining associated location data from the location device, matching previous and current rail condition data representing the realignment object. The steps further include calculating a location offset value based on the difference between associated previous and current location data, and applying the location offset value in comparing previous and current rail condition data to identify an indicator associated with the rail.

BRIEF DESCRIPTION OF THE DRAWINGS

FIG. 3 (FIGS. 3A, 3B, and 3C) depict a flow chart showing select steps performed in connection with the present rail inspection system;

FIG. 4 (FIGS. 4A, 4B, and 4C) depict a flow chart showing select steps performed in connection with the present rail inspection system;

DETAILED DESCRIPTION

Throughout this application, the use of the term "a," "an," or "the," means "at least one" or "the at least one" as appropriate, unless otherwise specified. Also, it is noted that the described steps throughout this application need not be performed in the disclosed order.

Figure 1:
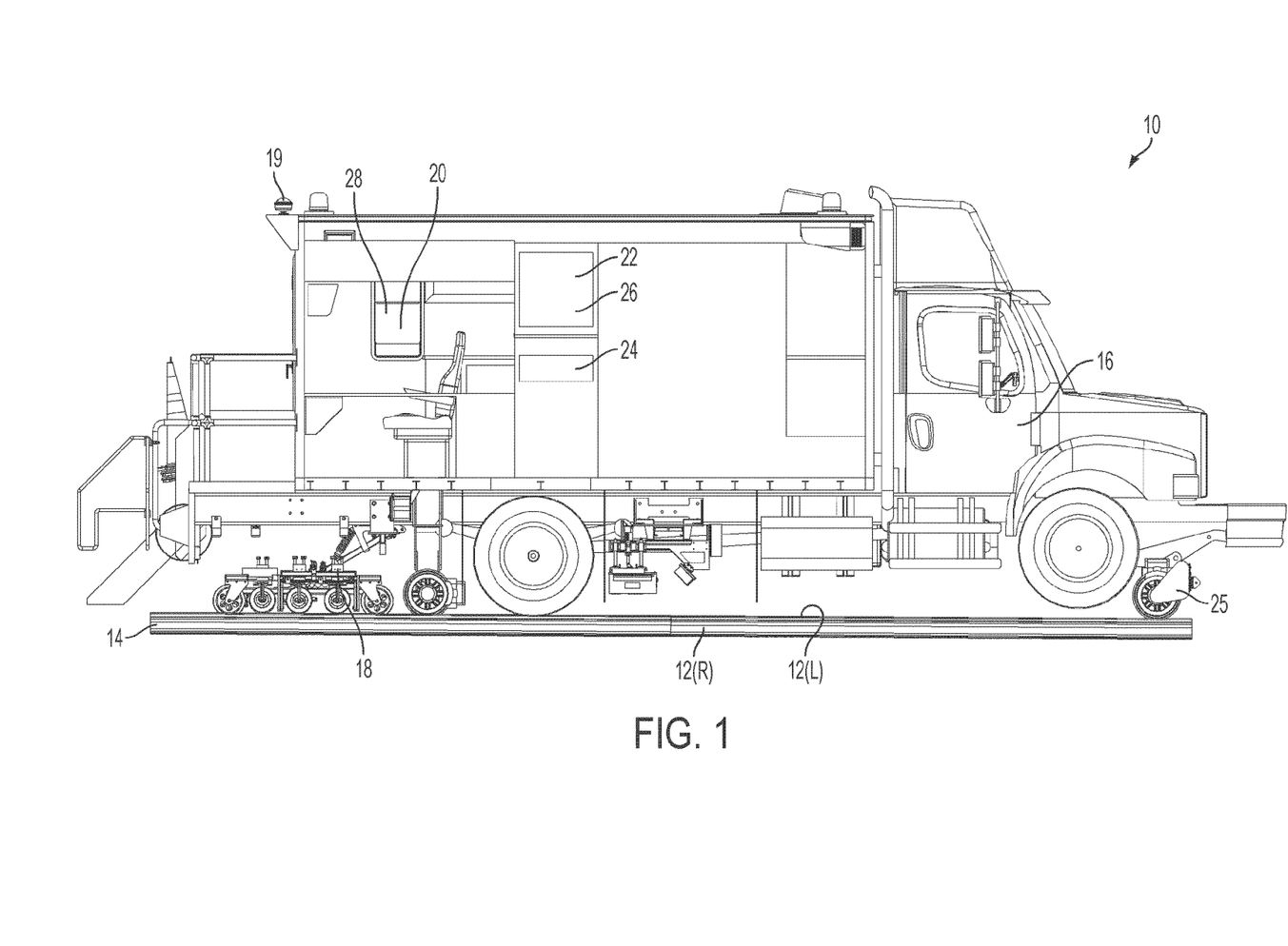
FIG. 1 is a front perspective schematic view of a preferred embodiment of the present rail inspection system.

Turning now to FIG. 1, a railway inspection system 10 for monitoring defects of a rail 12 portion of a railway 14 is shown. Since the railway 14 is typically built with two, generally parallel rails 12, connected to each other by a plurality of ties or sleepers (not shown), the preferred embodiment is configured to monitor defects of a left rail and a right rail simultaneously. Accordingly, while traditional reference numerals are used throughout this application to describe components/features of the present invention, "(L)" and "(R)" sub-designations are provided in the drawings to refer to components/features associated with the left and right rails, respectively (e.g., the rail 12 is referenced on the drawings as 12(L) and 12(R)). However, the present rail inspection system 10 is not limited to monitoring defects of two rails, but instead could be used for a single rail, or more than two rails depending on the desired configuration.

The system 10 includes an inspection vehicle 16 configured for traversing the rail 12, and a sensor 18 disposed on the vehicle and configured for obtaining rail condition data as the vehicle traverses the rail. Also disposed on the vehicle 16 is a location device 19 (e.g., a Global Position System or "GPS" device), a display device 20, a memory 22, a processor 24, an encoder 25, and a non-transitory computer-readable medium 26, all of which, along with the sensor 18, are electronically connected. The memory 20 is configured for storing previous rail condition data from a previous traversal of the rail 12 (described in greater detail below).

The computer-readable medium 26 contains instructions, which when executed by the processor 24, causes performance of a series of steps in real-time as the vehicle traverses the rail 12. As used throughout this application, the term "real-time" generally refers to a condition where events occur in actual, live, or substantially live time (i.e., without significant delay), as understood by those of ordinary skill in the art.

Figure 2:
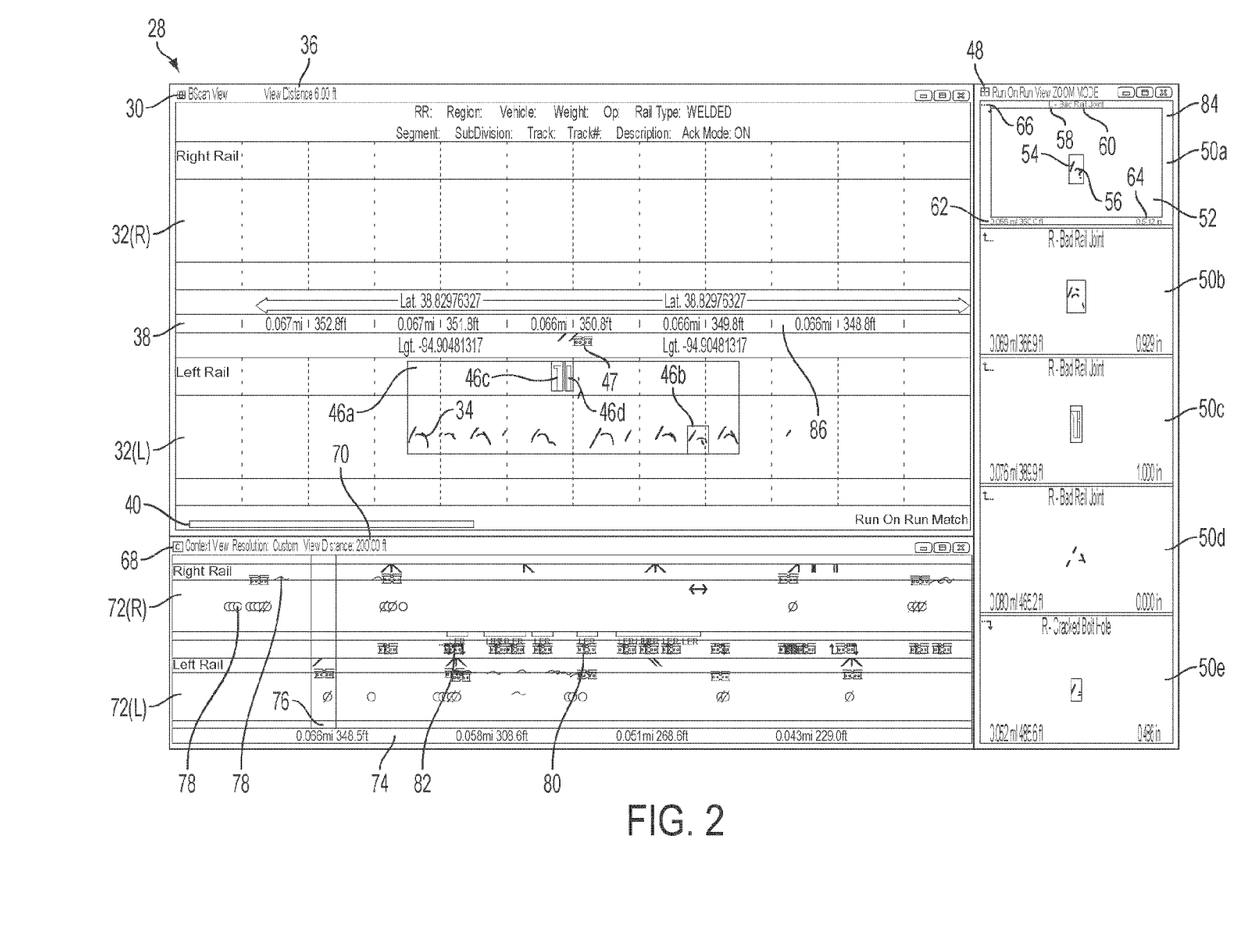
FIG. 2 is a first example screen shot of a user-interface of the present rail inspection system.

As select steps are performed, output is provided to the display device 20 via a user-interface 28, an example of which is shown in FIG. 2. The user-interface 28 is also configured to request and receive input from a user to cause performance of select steps. Accordingly, as components/features and corresponding steps of the present rail inspection system 10 are described, reference will be made to appropriate portions of the user-interface 28.

Figure 3A:
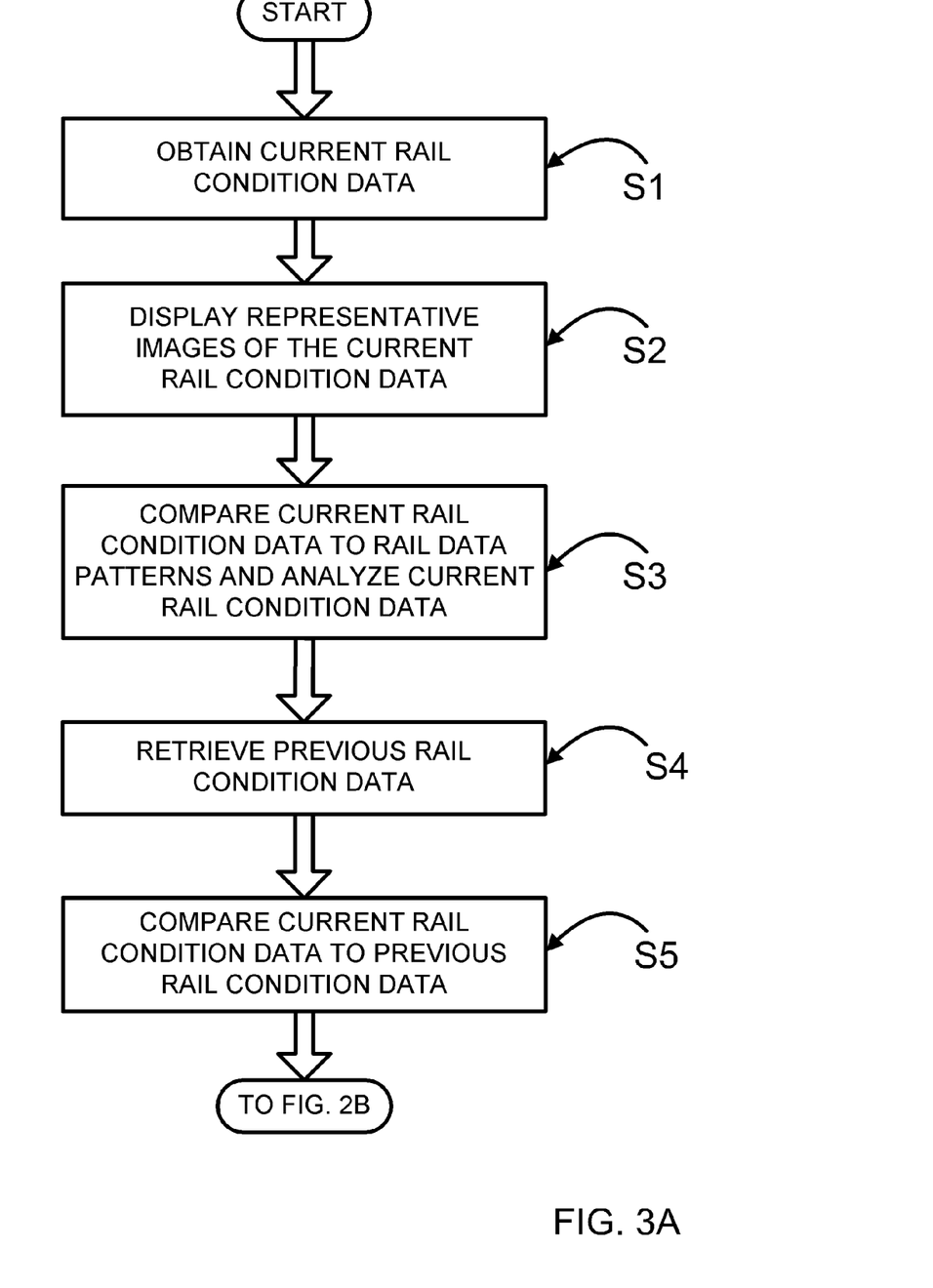
Figure 3B:
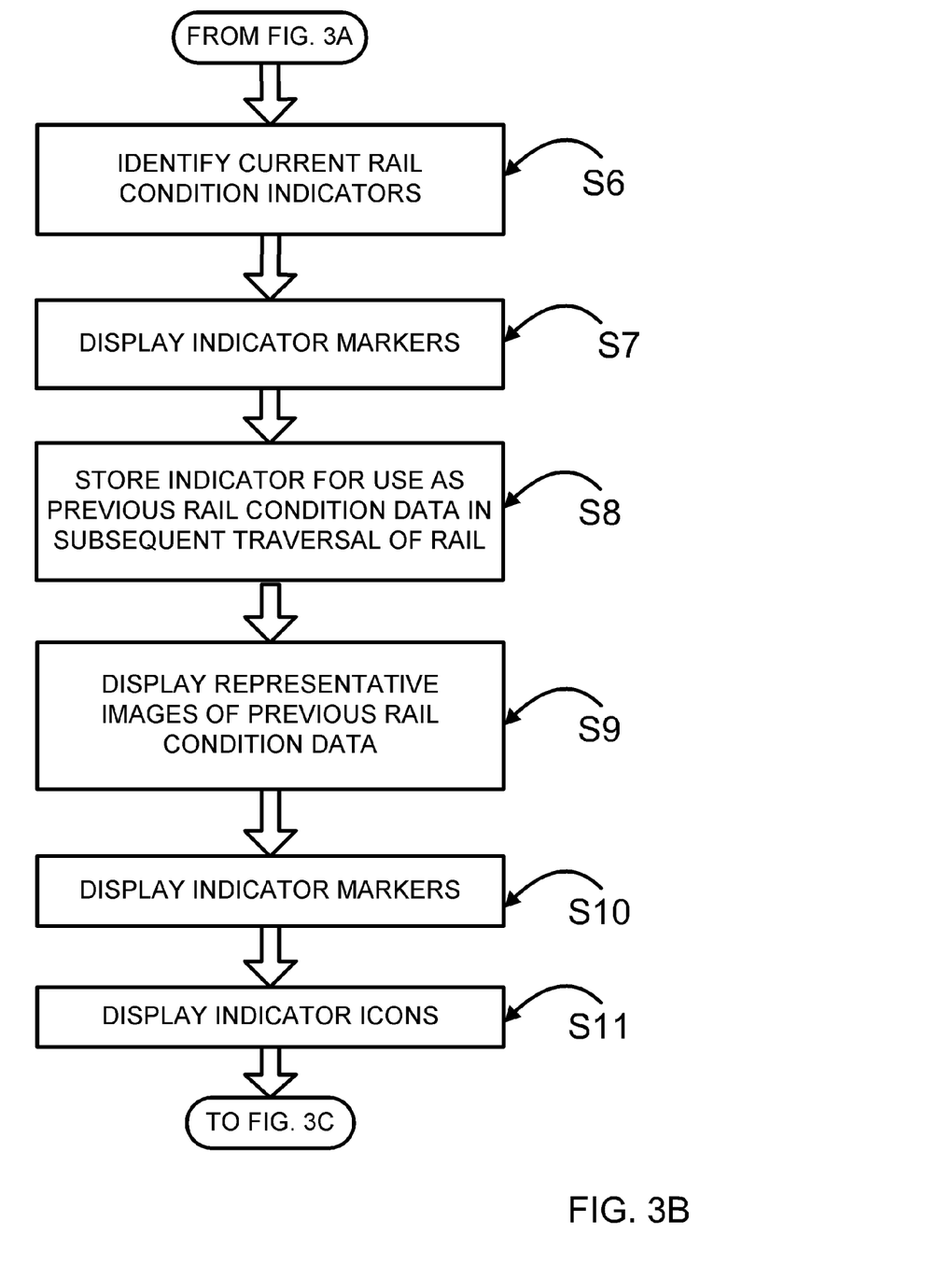
Figure 3C:
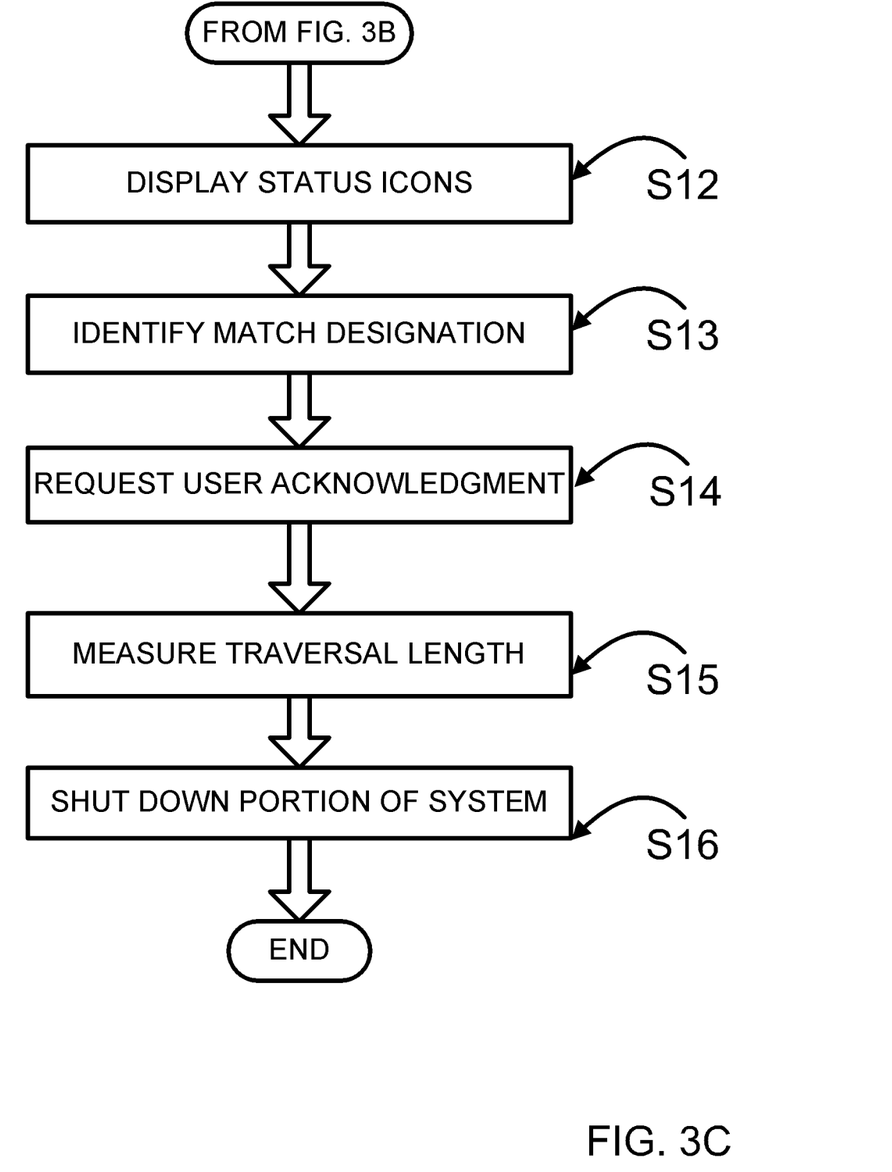

As shown in the flow chart of FIG. 3, in step S1, current rail condition data is obtained from the sensor 18. Since the described steps occur in real-time, this current rail condition data represents the "live" condition of the rail 12. Notably, reference to the term sensor 18 throughout this application optionally refers to a single sensor, or a plurality of sensors of one or many different types depending on the desired configuration. As in traditional and other known systems, in a preferred embodiment, one such sensor 18 uses ultrasonic signals to obtain the current rail condition data, but other types of sensors are contemplated. Additional sensors 18 are also contemplated for measuring tolerance, gain value, and outside temperature to obtain rail condition data that more accurately represents the condition of the rail 12. Since a lower outside temperature is expected to result in a loss of measureable sound (i.e., gain value), comparative techniques based on these measurements are optionally employed to obtain additional rail condition data (or improve the accuracy of other gathered data).

A current data window 30 of the user-interface 28 includes a rail representation area 32 configured to show representative images 34 of the current rail condition data. The current data window 30 has a view distance (i.e., a length of the portion of the rail 12 that is represented at one time by the representative images 34) that is configurable, and may depend on the type, location, and number of sensors 18 used, but in a preferred embodiment is approximately six feet. The view distance is shown in the current data window 30 in a view distance field 36. A location bar 38 having distance markers (from a predetermined starting point on the rail 12), and latitude and longitude coordinates, is also included for providing reference points for the current rail condition data and corresponding representative images 34. Further included in the current data window 30 is a scroll bar 40, which allows the user to view representative images 34 of different portions of the current rail condition data (representing different portions of the rail 12) if desired. In a preferred embodiment, the representative images 34 automatically propagate (i.e., from right to left) through the rail representation area 32 based on the location of the vehicle 16 as determined by the location device 19 (i.e., to avoid the need for constant scrolling by the user as the vehicle traverses the rail 12).

Figure 5:
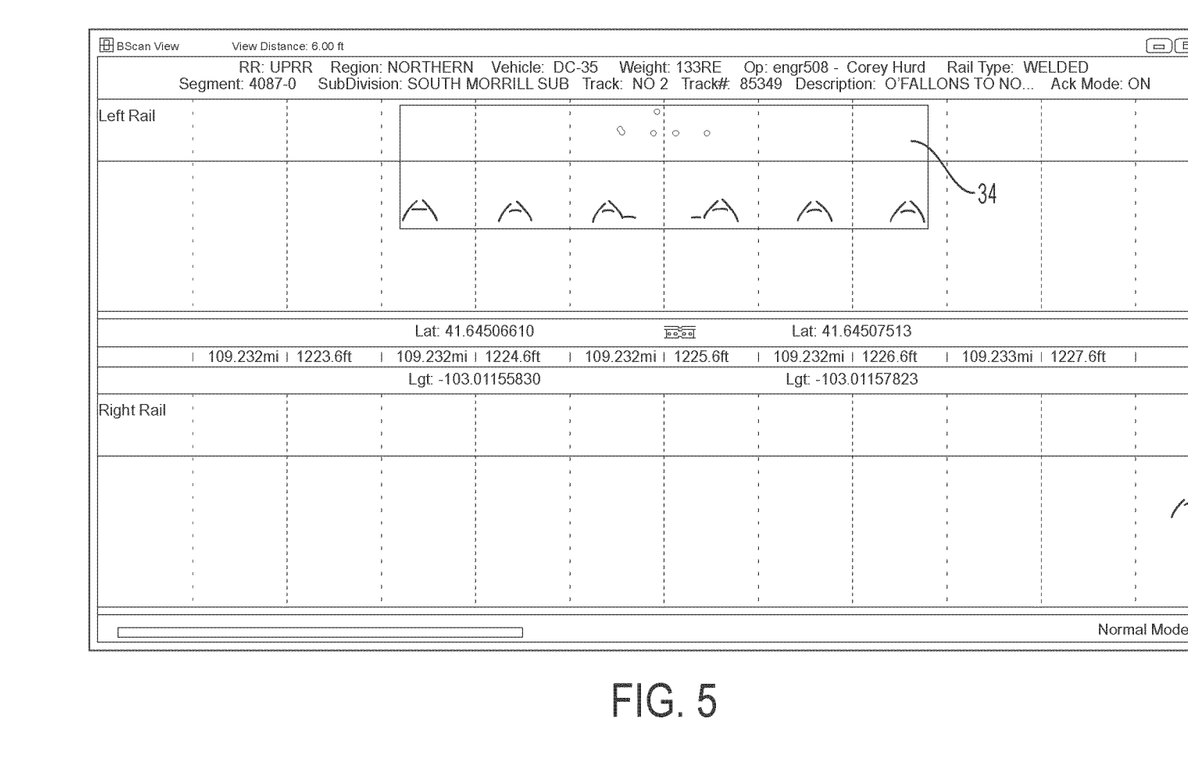
FIG. 5 is a second example screen shot of a rail representation area of a user-interface.
Figure 6:
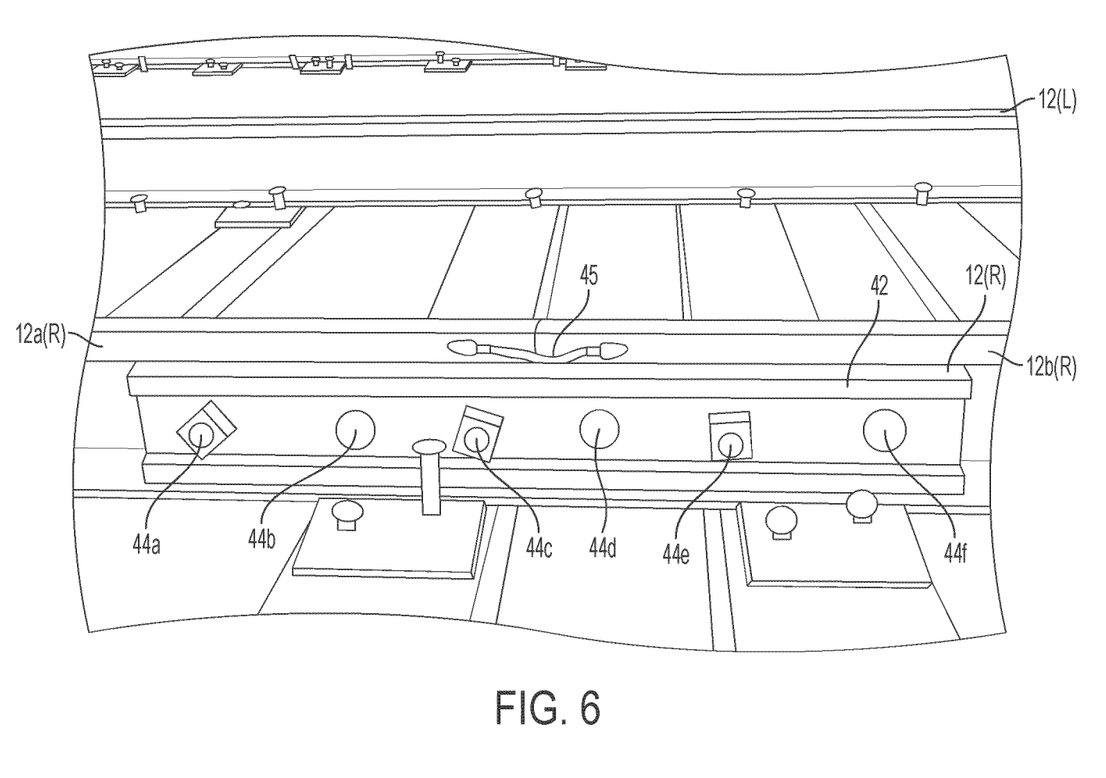
FIG. 6 is a top perspective view of a rail having a six hole joint that corresponds to the rail representation area shown in FIG. 5.

In step S2 representative images 34 of the current rail condition data are displayed on the display device 20 (via the user-interface 28 as described above). A second example illustration of the representative images 34 is shown in greater detail in FIG. 5, and a perspective top view of the corresponding portion of the rail 12 is seen in FIG. 6. The portion of the rail 12 shown in FIG. 5 depicts a common configuration of a six hole joint 42 having six corresponding bolts 44(*a-f*) and bolt holes (hidden) to fasten the joint to abutting ends of two sections 12*a*, 12*b* of the rail. As the vehicle 16 traverses the rail 12, the ultrasonic signals are transmitted to the rail and reflect back, and the other measurement data is gathered to generate the current rail condition data and corresponding representative images 34 of the bolt holes in FIG. 6. Notably, due to the position of the sensor 18 being disposed above the bolts 44 as the vehicle 16 traverses the rail 12, typically the ultrasonic signals only provide for an outline of approximately the upper half portion of the bolt holes. Referring again to the rail representation area 32 of FIG. 5, additional representative images 34 are also shown (in this example, as small circles) that correspond to a rail crown or head 45, disposed above the six hole joint 42 on the rail 12 as shown in FIG. 6.

In step S3, the current rail condition data is compared to a list of known rail data patterns (preferably stored in the memory 22) representing various types of rail components or properties (e.g., a six hole joint, a bolt hole, etc.), and/or is analyzed unilaterally based on its pattern (i.e., without a comparison). In addition, in step S4, previous rail condition data is retrieved from the memory 22, and in step S5, the current rail condition data is compared to previous rail condition data (i.e., data obtained from a previous traversal of the same portion of the rail 12) to provide a real-time "run-on-run" comparison of data. This feature is described in greater detail below following a description of the additional relevant portions of the user-interface 28.

In step S6, an indicator based on the current rail condition data is identified (i.e., where a recognized pattern match is found, where the unilateral pattern analysis yields a particular result, and/or based on a result of the "run-on-run" comparison of data). In step S7, the indicators are displayed on the display device 20 (via the user-interface 28 with an indicator marker 46). As shown in FIG. 2, in one example, the indicator markers 46 are boxes that enclose the representative image 34 of the corresponding portion of the rail condition data for which an indicator was identified. Notably, indicator markers 46 may also be nested as shown in FIG. 2, wherein one indicator marker 46*a* encloses the representative images 34 corresponding to an entire six hole joint, while a another indicator marker 46*b* encloses representative images corresponding to a single bolt hole with that six hole joint, and two additional indicator markers 46*c, d* enclose representative images respectively corresponding to the rail web and the rail foot or base.

By comparing the current rail condition data to the list of known rail data patterns and/or analyzing it unilaterally based on its pattern, potential defects of the rail 12 may also be determined. As such, the indicators may not only identify a type of rail component or property, but may also identify whether it has an associated defect, and the level of severity of that defect. In a preferred embodiment, the indicator markers 46 are color coded to provide such information. For example, an indicator marker 46 shown in green signifies that the corresponding portion of the rail 12 was recognized, but that it has no potential defect. Likewise, an indicator marker 46 shown in yellow signifies that the portion of the rail 12 was recognized, but that no conclusion was reached concerning the level of severity of a potential defect, or that the potential defect is not considered severe. Finally, an indicator marker 46 shown in red signifies that the portion of the rail 12 was recognized, and that it contains a severe defect.

The determination of whether an indicator signifies a severe defect is preferably based on use of a scoring technique, whereby the comparison of the current rail condition data to the list of known rail data patterns and/or the unilateral analysis based on its pattern, results in a quantifiable score that is compared against a predetermined threshold value. Notably, other colors and/or designations for the indicator markers 46 are also considered and could be used, for example, to indicate that a portion of the rail 12 is recognized and does not present a traditional defect, but is nonetheless out of position.

Finally, in a preferred embodiment, the user-interface 28 also includes an indicator icon 47 to represent the types of rail component or property associated with the indicator. Indicator icons 47 may represent a type of defect, including for example, a vertical split head, cracked bolt hole, etc., or may indicate some other rail property or component, including for example a bridge or grease on the rail. Indicator icons 47 may be determined automatically (i.e., as part of the pattern analysis) or selected by a user via an input through the user-interface 28.

If an indicator is identified wherein a corresponding defect is determined to exceed a predetermined threshold value (e.g., as discussed above as a condition to setting the indicator marker 46 color to red), in step S8, the indicator is stored (preferably in the memory 22) for use as previous rail inspection data during a subsequent traversal of a vehicle 16 over the rail 12. In alternative embodiments, all indicators are stored for use as previous rail condition data. The stored indicator preferably also includes related data such as, for example, a rail identifier (e.g., left or right), a location, a size (length), and a description of the corresponding indicator. The related data further includes any resulting actions taken by the user and any associated observations or comments provided by the user. In a preferred embodiment, such related data includes a user's selection from a plurality of status icons to represent an action taken or an observation made by the user. Such status icons may include, for example, a negative hand test icon representing that the corresponding portion of the rail 12 was physically inspected, but that no defects were found. Other status icons may represent, for example, a confirmation as to why the indicator was identified (e.g., due to grease on the rail, a bridge, etc.). In yet another example, a user may select an up or down arrow (referring to the passenger or driver's side respectively), merely indicating that the corresponding portion of the rail 12 should be considered on the next rail traversal.

Turning back to FIG. 2, the user-interface 28 further includes a previous data window 48 for showing data based on a previous traversal of vehicle 16 over the rail 12 as described above. The previous data window 48 includes an indicator module 50 which, similar to the current data window 30, includes a rail representation area 52 configured to show representative images 54 of the previous rail condition data (i.e., the stored indicators) and corresponding indicator markers 56. The indicator module 50 further includes fields for showing a rail identifier 58 (e.g., "L" for left or "R" for right), a description 60 (e.g., "bad rail joint"), a location 62, and a size 64 of the corresponding indicator. Further, the indicator module 50 includes a status icon 66 selected by a user during a previous traversal of the rail 12.

In the example shown in FIG. 2, the status icons 66 shown are the up and down arrow icons as described above.

Preferably, the previous data window 48 includes five indicator modules 50a-e configured to show the data related to the indicators stored as previous rail condition data in sequence (geographically) based on the current location of the vehicle 16, which updates in real time as the vehicle 16 traverses the rail 12. Accordingly, the indicator modules 50 provide the user with an overview of the next five upcoming indicators stored during the previous traversal of the rail 12 (for clarity, FIG. 2 only includes reference numerals for the features/components of the first of the fives indicator modules 50). While the preferred embodiment includes five indicator modules 50, more of less may be used depending on the desired configuration. In alternative embodiments, particularly where all indicators are stored for use as previous rail condition data (i.e., not just those where a corresponding defect is determined to exceed a predetermined threshold value), the previous data window 48 is optionally configured similar to the current data window 30, wherein the representative images 54 and corresponding indicator markers 56 are shown for all indictors of the previous rail condition data based on the same or a similar view distance used for the current data window.

Figure 4A:
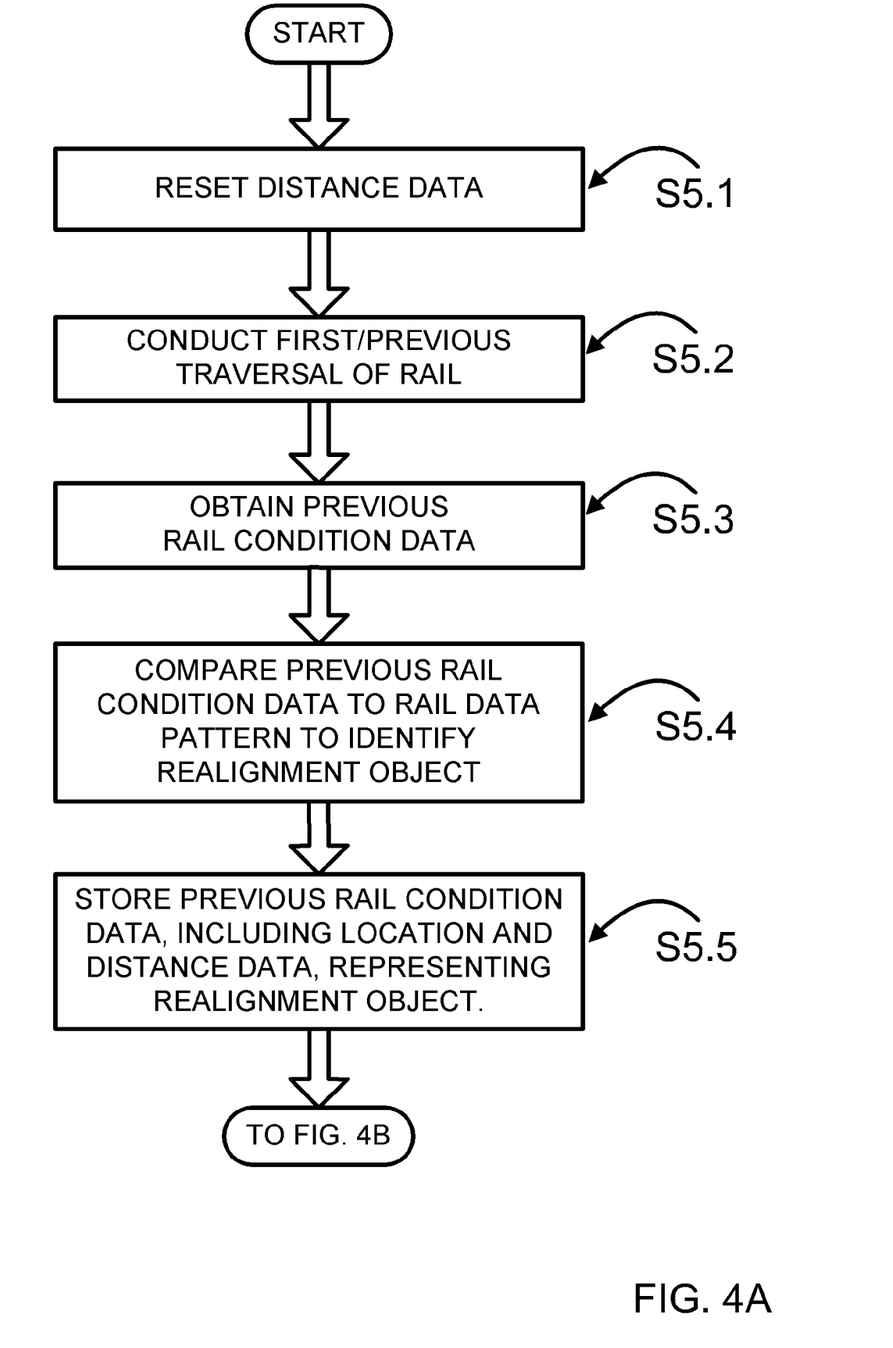
Figure 4B:
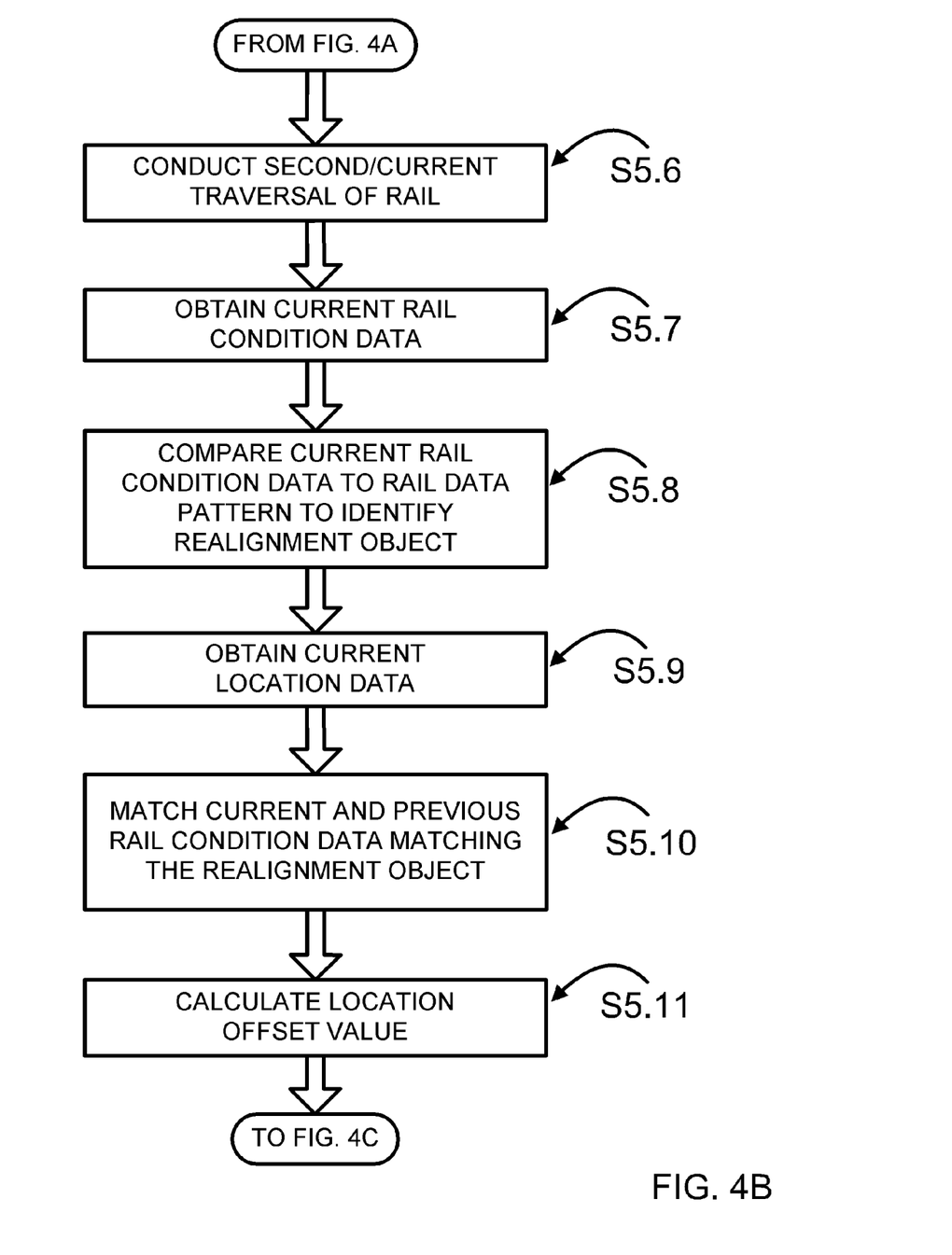
Figure 4C:
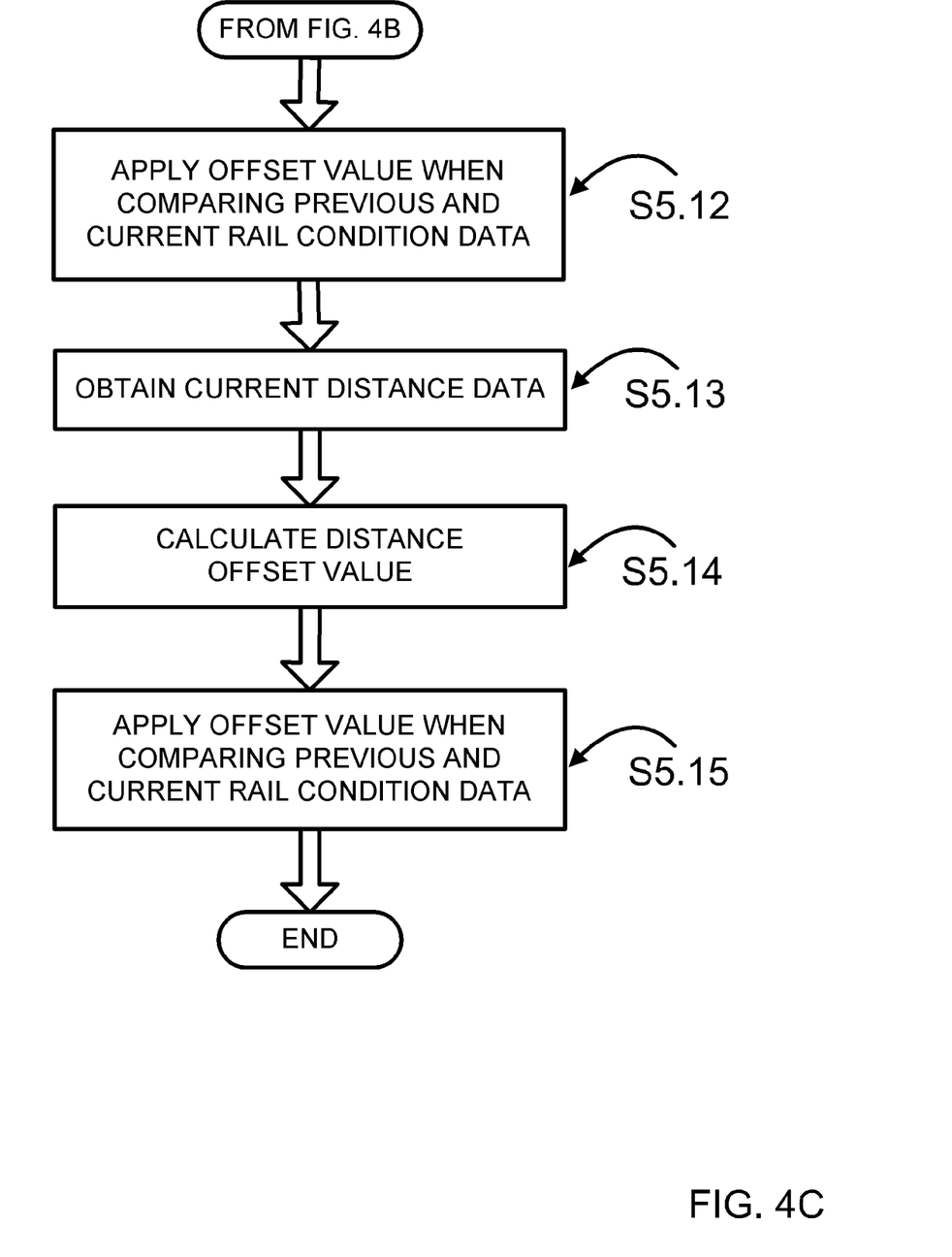

Based on the above description, it can be understood that in step S9, representative images of the previous rail condition data are displayed on the display device 20, and in step S10, the corresponding indicator markers 56 are displayed on the display device (both via the user-interface 28 as described above). Notably, the module 50 is configured to display the image so that it can be zoomed in and out such that a user can, for example, view representative images 54 of an entire six bolt hole, with the option to zoom in and show a representative image for a particular bolt hole (as shown in FIGS. 2 and 4). This zooming feature provides the user with an improved opportunity to analyze previous rail condition data to guide further action as described in greater detail below.

Referring still to FIG. 2, the user-interface 28 further includes a context data window 68, which, similar to the current data view window 30, includes a view distance field 70, a rail representation area 72, and a location bar 74. Preferably, the view distance of the context data window 68 is significantly larger than the view distance of the current data window 30 (e.g., two hundred feet as compared to six feet as shown in FIG. 2), such that the former provides a high level overview of a large portion of the rail 12 to the user. A vertical stripe 76 extending across a portion of the rail representation area 72 corresponds to the same portion of the rail 12 being represented in full in the current data window 30.

However, unlike the rail representation area 32 of the current data window, the rail representation area 72 of the context data window 68 does not include representative images, but instead includes only indicator icons 78 (that correspond to the indicator icons 47 in the current data window 30). The context data window 68 further includes an action bar 80 for showing status icons 82 (that correspond to the status icons 66 in the previous data window 48). Based on the above description, it can be understood that in step S11, indicator icons corresponding to the previous rail condition data are displayed on the display device 20, and in step S12, status icons corresponding to the previous rail condition data are displayed on the display device, both via the user-interface (e.g., in locations 47, 78, and 66, 82, respectively). It is noted that the user-interface 28 may contain additional fields for displaying select environmental or project related data to the user, including for example geographical indicators, project codes, and the like. Further, since the user-interface 28 is configured to request and receive input, it also contains traditional input means such as selectable buttons and drop down file menus.

Having now described the current data window 30, the previous data window 48, and the context data window 68 in the user-interface 28, a further description of step S5, wherein current rail condition data is compared with previous rail condition data, is provided. While the rail inspection system 10 provides access to both the current rail condition data (obtained in real-time from the sensor 18), and the previous rail condition data (retrieved from the memory 22 after being stored during a previous traversal of the rail 12), the data likely covers extensive portions of the rail 12. Accordingly, it is preferred that select techniques be implemented to provide for a proper comparison of appropriate and corresponding portions of the data to allows for the effective identification of indicators as previously described in step S6.

In a preferred embodiment, the current rail condition data includes location data acquired from the location device 19 and distance data (i.e., a distance traveled based on the number of "pulses" or counts representing a predefined distance traveled by the vehicle 16 over the rail 12 as read by the encoder 25, and potentially via the sensor 18). Since the previous rail condition data also includes such location and distance data (as it is essentially "old" current rail condition data), the two sets of location data can be considered and compared to ensure that the appropriate portions of the current and previous rail condition data are being compared for purposes of identifying an indicator. In another technique, realignment objects are considered to align the current and previous rail inspection data (i.e., to ensure that data representing the same physical portion of the rail 12 is being compared).

A preferred technique of aligning and comparing previous and current rail condition data where realignment objects are considered is now described with reference to FIG. 4 and shown in steps S5.1 through S5.15. Notably, some of the steps shown in FIG. 4 may be duplicative of other steps described throughout this application, but are included to clarify the features of the disclosed technique. In step S5.1, distance date (i.e., a distance counter) associated with the encoder 25 on the vehicle 16 is reset and is configured to count as the vehicle 16 traverses the rail 12 (preferably the encoder 25 is coupled to the sensor 18 such that the distance counter can increase based on the received ultrasonic signals indicating travel). In step S5.2, the vehicle 16 conducts a first traversal of the rail 12 (for clarity, the modifier "previous" is used in connection with data and actions associated with the first traversal of the rail, and the modifier "current" is used in connection with data and actions associated with a second traversal of the rail). In step S5.3, previous rail condition data is obtained from the sensor 18 as the vehicle 16 traverses the rail 12. In step S5.4, the previous rail condition data is compared to a rail data pattern as the vehicle 16 traverses the rail 12 to identify a realignment object, wherein the rail data pattern represents a predefined realignment object, which preferably includes an object, component, or characteristic of the rail 12 that has a low probability of changing as a result of subsequent rail traversals (e.g., bolt holes, rail joints, etc.). A realignment object should be contrasted with a defect (which is likely to increase in severity as a result of subsequent traversals) as described above.

For each realignment object that is identified, in step S5.5, previous rail condition data representing the alignment object is stored in the memory 16. Further included in the previous rail condition data and stored in the memory 16 is associated previous location data (e.g., longitudinal and latitudinal coordinates), which is obtained from the location device 19, and associated previous distance data (i.e., based on the distance counter), which is obtained from the encoder 25. The previous rail condition data is then utilized in a second (current) traversal of the rail 16 to ensure that appropriate portions of the previous rail condition data and being compared with appropriate portions of the current rail condition data (i.e., that the data representing the respective rails are being properly aligned with each other such that a proper comparison of data can be made).

As such, in step S5.6, the vehicle 16 conducts a second (current) traversal of the rail 12. It should be noted that the previous and current traversals of the rail may be performed by the same vehicle 16 or by two different vehicles. In step S5.7, current rail condition data is obtained from the sensor 18 as the vehicle 16 traverses the rail 12. In step S5.8, as with the previous rail condition data, the current rail condition data is compared to a rail data pattern to identify a realignment object as the vehicle 16 traverses the rail 12. For each realignment object that is identified, in step S5.9, associated current location data is obtained from the location device. Further, in step S5.10, previous rail condition data representing the realignment object is matched with current rail condition data representing the realignment object (tolerance values specifying a required degree of similarity or a distance range to be considered may be used to determine a match). In step S5.11, a location offset value (e.g., having longitudinal and latitudinal components) is calculated based on the difference between the previous location data associated with the realignment object (i.e. retrieved from the memory 16) and the current location data associated with the realignment object. Then, in step S5.12, the location offset value is applied when comparing further previous rail condition data to current rail condition data to identify indicators as the vehicle 16 traverses the rail 12. Preferably, the location offset value is recalculated each time a realignment object is identified such that the previous and current rail condition data is continually realigned to provide greater accuracy.

Application of the above-described technique aids in ensuring that a comparison between the previous rail condition data and the current rail condition data is based on a comparison of two sets of data corresponding to the same section of the rail 12. Since each in a given pair of GPS or other location devices, especially those with different model numbers and/or those made by different manufacturers, often provides slightly different results with respect to location data, the use of a location offset value (calculated as described above) effectively eliminates or at least reduces that difference in the obtained location data used to make further comparisons (i.e., to identify defect indicators) as described in greater details below.

While the above-described technique improves the comparison of previous rail condition data and current rail condition data, such an improvement is still limited by the precision level of the location device. Traditional GPS devices typically provide location data results that are accurate within a range of about three feet. More recent differential GPS devices increase this level of precision to approximately one inch. However, given the nature of rail defects, often an even greater level of precision is desired for an effective comparison of data obtained at different times for the same rail 12. As such, to further improve the above-described technique, distance data obtained from the encoder 25 is also considered. In particular, for each identified realignment object where previous rail condition data representing the realignment object is matched with current rail condition data representing the realignment object (as described above), in step S5.13, associated current distance data is obtained from the encoder 25. In step S5.14, a distance offset value is calculated based on the difference between the previous distance data associated with the realignment object (i.e., the distance between the vehicle's starting position on the previous traversal of the rail 12 and the previous distance data associated with the realignment object) and the current distance data. Then, in step S5.15, the distance offset value is applied when comparing further previous rail condition data to current rail condition data to identify indicators as the vehicle 16 traverses the rail 12.

Preferably, the distance offset value is recalculated each time a realignment object is identified. Further, in the event that the vehicle 16 performs one of a predefined set of actions, a flag is set such that the distance offset value is not applied, but instead only the location offset value is applied (until another realignment object is identified on the current traversal and the distance offset value is calculated again). For example, such actions may include when the vehicle stop and restarts, or where the vehicle moves in reverse, as such actions have a tendency to disrupt an otherwise constant and accurate counting by the encoder, thereby causing the distance data to be less accurate. However, in the event one of the actions occurs, once the current traversal passes another realignment object, the distance offset value is reset and the high precision comparison of previous and current rail condition data continues. Notably, in the meantime, some level of alignment precision is still provided by way of the location offset value as discussed above.

As shown in the technique discussed above, the combined use of a location device and an encoder in the disclosed system 10 provides high levels of precision when comparing data representing two or more rails. Indeed, some encoders have precision levels of ⅛sth of an inch or better, which therefore allows data representing two or more rails to be aligned with corresponding levels of precision, thereby allowing for an improved ability to identify matching indicators.

Returning again to FIG. 3, it is preferred that a quantifiable score be determined when a comparison is made between current and previous rail inspection data in step S5. The score can similarly be compared against a predetermined threshold value, and may be used for, among other things, identifying an indicator and selecting an appropriate indicator marker to better inform the user of what actions are appropriate. Notably, since the comparison is between previous and current rail condition data, the scoring technique may differ from that used when the current rail inspection data is analyzed on its own (or as compared to known rail pattern data). For example, it may be desired to assign an indicator with a score signifying the existence of a severe defect even when only a moderate defect has been identified, if the comparison shows that the problem has become worse over time. Indeed, while the potential defect may not be technically considered severe yet, it may be recommended to preemptively address the defect before it develops into a more severe one.

In addition to showing the indicator markers 46, 56, it is also preferred that in step S13, a match designation for matching indicators of the current and previous rail condition data is displayed on the display device (via user-interface 28). In the example shown in FIG. 2, the location bar 38 in the current data window 30 and the appropriate indicator module 50 in the previous data window 48 are highlighted with a border 84, 86, respectively, to indicate the same. Such match designations are implemented to further assist the user in understanding and making decisions as to what actions to take (e.g., selecting an appropriate status icon 66).

In some instances, the rail inspection system 10 may also require user acknowledgement as shown in step S14. For example, if the quantified score for an indicator (regardless of how it was identified) exceeds a predetermined threshold value, a request for user acknowledgement is made on the display device 20 (i.e., via the user-interface 28). In a preferred embodiment, once a request for user acknowledgement is made, in step S15, a traversal length of the vehicle 16 starts to be measured. Then, if the traversal length exceeds a predetermined acknowledgement length value (e.g., five hundred feet), in step S16, a portion of the system 10 (preferably, execution of further instructions contained on the computer-readable medium) is halted and temporarily shut down until the acknowledgement is received from the user. This feature ensures that users are being attentive and are actively monitoring the user-interface 28 as the vehicle 16 traverses the rail 12. Indeed, if a user completely stops monitoring the user-interface 28 and indicators are identified that require user acknowledgement, a portion of the system will eventually shut down forcing the user provide an acknowledgement.

By displaying data relating to both the current and previous rail condition data in real time as described throughout this application, a user is able to reduce the need to stop and re-start traversal of the vehicle 16 along the rail 12, and is further able to make more informed decisions about what actions to take and to more accurately identify portions of the rail requiring repair as the vehicle traverses the rail, thereby alleviating the need for a second traversal as required in traditional or other known system. It should also be noted that the present rail inspection system 10 is not limited to the use of previous rail inspection data based on a single previous traversal over the rail 12. Indeed, in some embodiments the previous rail inspection data stored in the memory 22 on the vehicle 16 may include data obtained from multiple traversals of the corresponding portion of the rail 12. Such data in particularly beneficial when current and previous rail condition data is being compared for the purpose of determining whether a potential defect is becoming worse over time, and thereby provides for a more accurate determination of a quantifiable score for an indicator.

It is also noted that while the previous rail condition data is stored in a memory 22 onboard the vehicle 16 such that the "run-on-run" comparison and other described steps can be performed in real-time, preferably the vehicle 16 is equipped with means for easily transporting such data to and from the memory (e.g., via a removable memory drive), or through a wireless communication device onboard the vehicle (e.g., a device with a cellular or a WiFi connection) such that the previous rail inspection data can easily be transferred, stored, or achieved. Among other things, such a feature allows for vehicles to be exchanged (e.g., due to a mechanical defect), without concern for which vehicle has the proper previous rail inspection data for the particular portion of the rail 12 (as the data can easily be transferred). Further, real-time wireless communication to the vehicle 16 allows a remote quality auditor to monitor activity of a vehicle (and actions taken by a user) for evaluation purposes, or to provide feedback, or support to the user. For storage or archival purposes, in some embodiments, it is also contemplated that a collection of rail inspection data is primarily maintained on a remote server, the relevant portion of which is then transferred to particular vehicles 16 as needed for traversal of a particular portion of a rail 12. Such data is preferably stored a using geo-hashing or geo-spatial file organization (i.e., database), but other such fie organization techniques may also be employed.

In other embodiments, the wireless communication device enables a remote user to enhance the "run-on-run" comparison technique by comparing the current rail condition data with several instances of previous rail condition data (stored remotely) while the vehicle 16 traverses the rail 12. As a result, the remote user can communicate with the user on the vehicle 16 to provide further details and/or recommendations with respect to the current rail condition data. In addition, the remote user can directly manipulate and/or supplement the current rail condition data to aid the user on the vehicle 16 (e.g., by setting a flag to highlight a specific area of concern).

While particular embodiments of the present rail inspection system have been described herein, it will be appreciated by those skilled in the art that changes and modifications may be made thereto without departing from the invention in its broader aspects and as set forth in the following claims.

The invention claimed is:

1. A railway inspection system for monitoring a defect of a rail, comprising:
    an inspection vehicle configured for traversing the rail;
    a sensor disposed on said vehicle and configured for obtaining rail condition data;
    a memory disposed on said vehicle and storing previous rail condition data from at least one previous traversal of the rail;
    a display device disposed on said vehicle;
    a processor disposed on said vehicle; and
    a non-transitory computer-readable medium, disposed on said vehicle, and containing instructions, which when executed by said processor, causes performance of the following steps in real-time as said vehicle traverses the rail:
        obtaining current rail condition data from said sensor;
        displaying on said display device representative images of said current rail condition data;
        retrieving said previous rail condition data from said memory;
        displaying on said display device representative images of said previous rail condition data compared with said current rail condition data;
        providing a real-time comparison of said previous rail condition data and said current rail condition data on said display device;
        comparing said current rail condition data to known rail data patterns;
        identifying a current rail condition indicator marker associated with said defect based on said comparison between said current rail condition data to said known rail data patterns;
        displaying on said display device a first indicator marker corresponding to said current rail condition indicator and a second indicator marker corresponding to an indicator provided in said previous rail condition data;
        determining a quantifiable score based on said current rail condition data and said known rail data patterns, representing said current rail condition indicator marker using said quantifiable score and displaying a user acknowledgement request on said display device when said quantifiable score for said current rail condition indicator exceeds a predetermined threshold value;
        separately providing a current data window and a previous data window for simultaneously displaying both said current and previous rail condition data for comparison of said first and second indicator markers; and
        associating a color with said first indicator marker, wherein said color indicates the severity of said defect based on said quantifiable score,
        displaying on said display device a match designation, if said current rail condition indicator matches said second indicator marker; and
        measuring a travel distance of the vehicle since said request for user acknowledgement was made, and if said travel distance exceeds a predetermined length value and said user acknowledgement is not received, halting a portion of said system until said user acknowledgement is received,
    wherein said sensor, said memory, said display device, said processor, and said computer-readable medium are electronically connected.

2. The railway inspection system of claim 1, wherein said non-transitory computer-readable medium is further configured to perform the following steps in real-time as said vehicle traverses the rail:
    analyzing said current rail condition data unilaterally;
    identifying said current rail condition indicator based on said analysis; and
    displaying on said display device said indicator marker corresponding to said current rail condition indicator.

3. The railway inspection system of claim 1, further comprising a location device configured for obtaining said location data based on a location of said vehicle.

4. The railway inspection system of claim 3, wherein said non-transitory computer-readable medium is further configured to perform the following steps in real-time as said vehicle traverses the rail:
    displaying on said display device a status icon corresponding to said previous rail condition indicator.

5. The railway inspection system of claim 3, wherein said non-transitory computer-readable medium is further configured to perform the following steps in real-time as said vehicle traverses the rail:
    displaying on said display device an indicator icon corresponding to said previous rail condition indicator.

6. The railway inspection system of claim 1, wherein said railway inspection system further includes a wireless communication device, and wherein said non-transitory computer-readable medium is further configured to transfer previous rail condition data from a remote server to said memory for storage via said wireless communication device.

7. The railway inspection system of claim 1, wherein said sensor employs ultrasonic signal and measures tolerance, gain value, and temperature levels of portions of the rail to obtain said current rail condition data.

8. The railway inspection system of claim 1, wherein said non-transitory computer-readable medium is further configured to perform the following steps in real-time as said vehicle traverses the rail:
    receiving a user selection of a status icon corresponding to said current rail condition indicator.

* * * * *